United States Patent [19]

Barr

[11] Plant 5,050

[45] May 10, 1983

[54] APPLE TREE

[75] Inventor: Annette Barr, Yakima, Wash.

[73] Assignee: McCormick Fruit Tree Co., Inc., Yakima, Wash.

[21] Appl. No.: 298,901

[22] Filed: Sep. 2, 1981

[51] Int. Cl.[3] ..... A01H 5/00
[52] U.S. Cl. ..... Plt./34
[58] Field of Search ..... Plt./34

*Primary Examiner*—James R. Feyrer
*Attorney, Agent, or Firm*—Frank B. Robb

[57] ABSTRACT

An apple tree which closely resembles the usual Jonathan in form and size, producing fruit having the color and shape of Starking Delicious (unpatented) but actually tasting and having the texture of Jonathan, with improved sugar content at comparable stage of development and good keeping qualities.

2 Drawing Figures

My present invention relates to a new variety of apple tree which I discovered as a chance seedling growing near some old trees which were saved when the other trees in an old section of former cultivated family orchard, were removed to provide an area for farming.

The initial discovery was thought at first to merely constitute another Red Delicious, since the trees in the area formerly growing there, were of the old Starking (unpatented) variety, the fruit appearing at that time to be colored and shaped like the fruit from those trees would be expected to appear.

However when the fruit was used for cooking and tasted, it was found to have the distinct flavor and texture of a Jonathan apple.

The foregoing led to closer observation and careful comparison which produced the conclusions that the fruit did in fact combine many aspects of the two old well known varieties including an even more intense red than the Starking Delicious with definite shape thereof however being retained.

When used for cooking and eating the decided Jonathan flavor was evident.

Testing of the fruit was effected because of our orchard experience and resulted in establishing a number of outstanding average aspects including a substantially greater sugar content at the same stage of development that the parent varieties, greater pressure test score, somewhat lower acid content, and total greater value because of excellent keeping qualities.

All of the foregoing support my decision to designate my new variety as "Deli-Jon" because of the combination of attributes of both Delicious and Jonathan varieties, and I have caused asexual reproduction to be effected, by budding in the vicinity of Zillah, Wash. finding that the improved characteristics and distinctions are retained and come true in successive propagations, assuring that an improved commercial variety has in fact been discovered and developed.

In summarizing the improvements and advantages of my new variety, the following appear to be the most outstanding:

1. Excellent color of an old variety of Starking Red Delicious.
2. Attractive shape of Starking.
3. Increased sugar content as compared with similar varieties.
4. Long keeping characteristics on the average 165 days in ordinary storage.

5. Resemblance of the tree to Jonathan.
6. Distinct flavor of the fruit more closely resembling Jonathan than Delicious.
7. Good resistance to apple diseases as well as mildew.

There follows a detailed description of my new variety as to tree and fruit, taken in conjunction with color illustrations of the same in the drawing, which discloses important aspects in color as nearly like that of the fruit and leaves, as is possible to provide the same in a color disclosure of this kind, color comparisons wet forth being made with the Nickerson Color Fan, published by Munsell Color Company where such comparisons are distinct and as to those aspects which may be described with common terms, ordinary descriptive language is used.

Locality where grown and observed: Zillah, Wash.

Date of first and last picking: September 25th and October 3rd.

Tree: Small size; medium vigor; spreading; low; open; slow growing; half hardy; medium productive.

*Trunk.*—Stock; medium.

*Branches.*—Medium; smooth; much branching. Color — brown. Lenticels — Medium and small.

Foliage:

*Leaves.*—Medium; (about 4 inches long — 2 6/10 inches wide) oval; abruptly pointed; medium thickness. Color — 10 Y 5/5 light olive. Margin — Coarsely serrate. Petiole — Length (1 7/10 inches); medium thickness.

Flowers:

*Dates of first and full bloom.*—About April 20th to April 25th.

*Size.*—Medium.

*Color.*—White.

Fruit:

*Maturity when described.*—Eating hard, October 3.

*Pectin.*—7 percent.

*Starch.*—Medium.

*Acid.*—0.39 percent.

*Brix.*—14.1 percent.

*Ph.*—3.7.

*Size.*—Axial diameter 3 2/10 inches. Transverse 3 inches.

*Form.*—Uniform; symmetrical; regular; oblong; conical. Five humps at blossom end.

*Cavity.*—Symmetrical. Depth — 6/10 inches. Breadth — 7/10 inches.

*Basin.*—Symmetrical; narrow; crowned.

*Stem.*—Stout; pubescent. Length — 9/10 inches. Bracts — few; about 5.

*Calyx.*—Closed; segments persistent; narrowly oblong. Length — 4/10 inches. Imbricate at base; inner and outer surface pubescent.

*Eye.*—Small; partially closed.

*Skin.*—Thick; tough; smooth; glossy; waxed. Dots — obscure; small; even; circular. Color — yellow-green. Distribution — scattered. Color markings — Blushed; bright. Ground color — Greenish yellow. Color of markings — All over red with few ground color spots. Bloom — scant; wanting; distribution — small. General color effect — Strong red 5 R 4/12, largely dependent upon manner in which light strikes the fruit.

Flesh: Juicy.

*Color.*—White.

*Texture.*—Hard; fine; crisp.

*Flavor.*—Subacid; sweet; sprightly; rich.

*Aroma.*—Distinct — more nearly like that of Jonathan.

*Quality.*—Best. Flesh stays white longer than Delicious — similar to Jonathan.

Core:

*Sessile.*—Medium.

*Bundle area.*—Medium; narrowly symmetrical.

*Halves of area.*—Equal.

*Bundles.*—Yellowish.

*Whorls.*—Two.

*Alternate bundle.*—Below stamens.

*Core lines.*—Meeting.

*In cross-section.*—Distinct.

*Carpellary area.*—Distinct; small.

*Calyx.*—Pubescent; cone-shaped.

*Stem of funnel.*—Short.

*Depth of tube to shoulder.*—3/10 inch.

*Entire depth.*—4/10 inch.

*Styles.*—10; distinct; toward base; pubescent.

*Stamens.*—Distinct. Whorls — basal.

*Auxillary cavity.*—Wanting.

*Seed cells.*—Closed. Cell walls — thick; tough. Length 7/10 inches. Breadth 4/10 inches. Longitudinal section — Oblong. Surface — Smooth. Cross-section — Narrow.

Seeds:

*Number.*—Perfect; 10.

*Number in one cell.*—2.

*Length.*—3/10 inches.

*Breadth.*—2/10 inches.

*Form.*—Acute.

*Color.*—2.5 YR 3/3 — Moderate reddish brown.

Use: Market; local; dessert; culinary.

Keeping quality: Good; about 165 days in ordinary storage.

Resistance to:

*Insects.*—Medium.

*Diseases.*—Good with resistance to mildew.

I claim:

1. A new and distinct variety of apple tree substantially as herein shown and described, characterized particularly as to novelty by the unique combination of attractive appearance in color and shape which closely resembles Starking Delicious (unpatented), while having the flavor and texture of Jonathan, as well as tree shape and size of Jonathan, improved sugar content, excellent keeping qualities, and good resistance to disease and mildew.

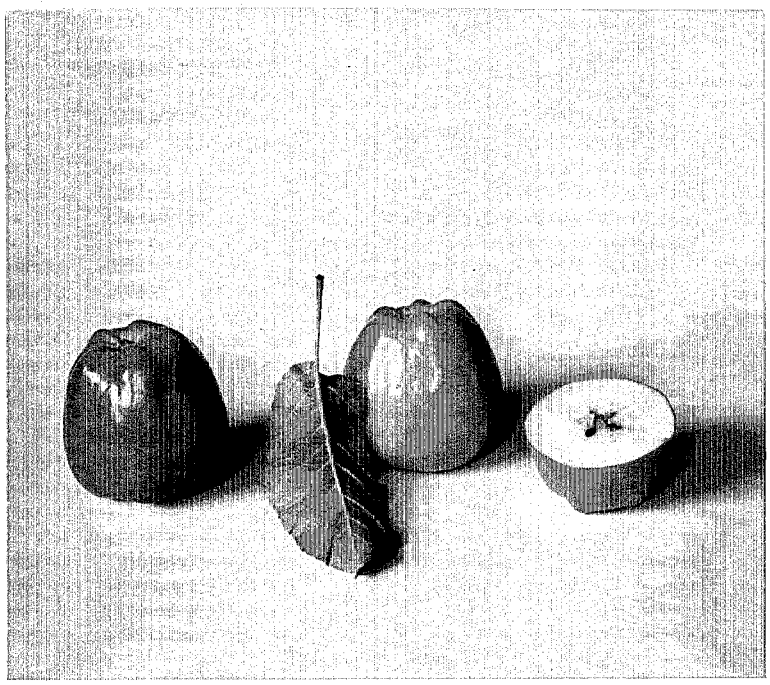
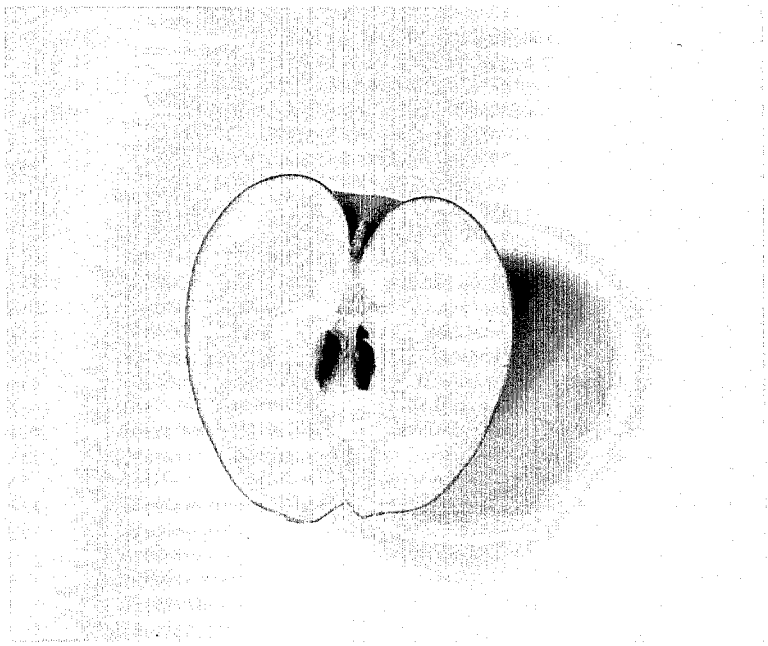

* * * * *